United States Patent
Jung et al.

(10) Patent No.: US 10,119,957 B2
(45) Date of Patent: Nov. 6, 2018

(54) MULTI-METABOLITES PLATFORM FOR DIAGNOSIS OF ACUTE CORONARY SYNDROME

(71) Applicant: KOREA INSTITUTE OF SCIENCE AND TECHNOLOGY, Seoul (KR)

(72) Inventors: Byung Hwa Jung, Seoul (KR); Jong Min Choi, Seoul (KR); Hong Seog Seo, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 459 days.

(21) Appl. No.: 14/795,163

(22) Filed: Jul. 9, 2015

(65) Prior Publication Data

US 2016/0305931 A1 Oct. 20, 2016

(30) Foreign Application Priority Data

Apr. 17, 2015 (KR) .................. 10-2015-0054597

(51) Int. Cl.
*G01N 33/49* (2006.01)
*G01N 33/68* (2006.01)

(52) U.S. Cl.
CPC ....... *G01N 33/492* (2013.01); *G01N 33/6893* (2013.01); *G01N 2405/02* (2013.01); *G01N 2405/04* (2013.01); *G01N 2405/08* (2013.01); *G01N 2570/00* (2013.01); *G01N 2800/324* (2013.01)

(58) Field of Classification Search
CPC ............. G01N 33/492; G01N 33/6893; G01N 2570/00; G01N 2800/324; G01N 2405/08; G01N 2405/04; G01N 2405/02
See application file for complete search history.

(56) References Cited

U.S. PATENT DOCUMENTS

| 2009/0269796 A1 | 10/2009 | Gerszten et al. |
| 2011/0137131 A1 | 6/2011 | Adourian et al. |
| 2013/0345581 A1 | 12/2013 | Body |

FOREIGN PATENT DOCUMENTS

KR 10-1051470 7/2011

OTHER PUBLICATIONS

Wong et al. (Journal of Chromatography B, 2008, 871:341-348) (Year: 2008).*
Marjani, Abdoljalal. "Serum fatty acid in patients with acute myocardial infarction in Gorgan." Al Ameen Journal of Medical Sciences 2012; 5(4): 342-346. (5 pages in English).
Ganna, Andrea, et al. "Large-scale Metabolomic Profiling Identifies Novel Biomarkers for Incident Coronary Heart Disease." PLOS Genet vol. 10, Issue. 12, Dec. 2014: e1004801: 1-10. (11 pages in English).

* cited by examiner

*Primary Examiner* — Jeremy C Flinders
(74) *Attorney, Agent, or Firm* — NSIP Law

(57) ABSTRACT

The present disclosure provides a multi-metabolite platform using one or more metabolite selected from a group consisting of tryptophan, homoserine, fatty acid (16:1), fatty acid (18:0), fatty acid (18:1), fatty acid (18:2), fatty acid (22:6), phosphatidylcholine (PC) (34:2), PC (34:3), lysophosphatidylcholine (lysoPC) (16:0), lysoPC (18:0), lysoPC (20:3), lysoPC (20:4), lysoPC (22:6), monoglyceride (18:1/0:0/0:0) and sphingomyelin (d18:2/16:0) as a biomarker, which can diagnose acute coronary syndrome as well as the symptoms occurring prior to the onset of the disease simply and accurately through in-vivo level analysis.

8 Claims, 14 Drawing Sheets

● Acute myocardial infarction group
▲ Normal control group
■ Unstable angina group ● Acute myocardial infarction group
▲ Normal control group
■ Unstable angina group

MULTI-METABOLITES PLATFORM FOR DIAGNOSIS OF ACUTE CORONARY SYNDROME

CROSS-REFERENCE TO RELATED APPLICATION

This application claims priority to Korean Patent Application No. 10-2015-0054597, filed on Apr. 17, 2015, and all the benefits accruing therefrom under 35 U.S.C. § 119, the contents of which in its entirety are herein incorporated by reference.

BACKGROUND

1. Field

The present disclosure relates to a multi-metabolite biomarker platform for diagnosis of acute coronary syndrome.

This study was supported by Projects No. CAP-12-1-KIST, No. 2E25360 and No. 2014048357 of Ministry of Science, ICT and Future Planning, Republic of Korea under the superintendence of Korean Institute of Science and Technology.

2. Description of the Related Art

Cardiovascular disease is the number one cause of death worldwide. According to the Statistics Korea, the number of the patients who died of cardiovascular diseases well exceeded that of the patients who died of cerebrovascular diseases since 2012. In particular, acute coronary syndrome (ACS), which includes acute myocardial infarction (AMI) and unstable angina, is the most frequent cause of emergency room visit by patients who complain of chest pain. Acute coronary syndrome is characterized by irreversible damage to the heart muscle cells due to decreased blood flow in the coronary arteries and insufficient oxygen supply to the heart muscle. In particular, acute myocardial infarction, with high lethality and mortality, accounts for 30% of the acute coronary syndrome. It is a lethal disease which is the number one cause of adult sudden death and is increasing gradually. Unstable angina is very dangerous even when the lesion size is small because of high risk of disruption of atherosclerotic plaques. However, it is difficult to be diagnosed only with symptoms such as chest pain and may develop into acute myocardial infarction or even cardiac arrest.

Unfortunately, however, it is very difficult to predict the likelihood of occurrence of acute myocardial infarction for unstable angina patients who visit emergency rooms due to chest pain or asymptomatic unstable angina patient. As such, it is difficult for a physician to determine whether an unstable angina patient will be hospitalized to see if acute myocardial infarction occurs. Therefore, development of a biomarker which is capable of diagnosing myocardial infarction early and predicting the change of unstable angina prior to the onset of myocardial infarction is urgent.

At present, glutamic oxaloacetic transaminase (GOT), lactate dehydrogenase (LDH), creatine kinase MB (CK-MB), troponin I, troponin T, C-reactive protein (CRP) and B-type natriuretic peptide (BNP) are used as biomarkers for the diagnosis of cardiovascular disease or heart failure. However, they are not biomarkers specific for myocardial infarction or unstable angina. In particular, although the troponin proteins are used for the diagnosis of myocardial infarction as markers of heart muscle cell necrosis, there are problems in that early diagnosis is difficult and stage-by-stage diagnosis from unstable angina to myocardial infarction is impossible.

Meanwhile, the detection of vulnerable plaques which frequently occur in unstable angina has been possible only with an invasive method such as intravascular ultrasound (IVUS) and a diagnosis method based on low-molecular-weight metabolites found in blood has never been attempted.

Accordingly, metabolites specific for acute myocardial infarction and unstable angina, which allow for fast and accurate detection of acute myocardial infarction and unstable angina and risk factors thereof in the early stage via a simple test and development of a platform for utilizing them for clinical diagnosis are necessary.

REFERENCE OF THE RELATED ART

Patent Document

US Patent Application No. 2013-0345581 (published on Dec. 26, 2013).

SUMMARY

The present disclosure is directed to providing metabolites specific for acute coronary syndrome as biomarkers. The present disclosure is also directed to providing a multi-biomarker platform for diagnosis of acute coronary syndrome at different stages by analyzing the in-vivo level of the metabolites.

In an aspect, the present disclosure provides a composition for diagnosis of acute coronary syndrome, containing a material for detecting one or more metabolite selected from a group consisting of tryptophan, homoserine, phosphatidylcholine (PC) (34:2), PC (34:3), lysophosphatidylcholine (lysoPC) (16:0), lysoPC (20:4), lysoPC (22:6), monoglyceride (18:1/0:0/0:0) and sphingomyelin (d18:2/16:0) as an active ingredient.

In another aspect, the present disclosure provides a composition for diagnosis of acute coronary syndrome, which further contains a material for detecting one or more metabolite selected from a group consisting of fatty acid (16:1), fatty acid (18:0), fatty acid (18:1), fatty acid (18:2), fatty acid (22:6), lysoPC (18:0) and lysoPC (20:3) as an active ingredient.

In another aspect, the present disclosure provides a kit for diagnosis of acute coronary syndrome, comprising an in-vivo level detector of one or more metabolite selected from a group consisting of tryptophan, homoserine, phosphatidylcholine (PC) (34:2), PC (34:3), lysophosphatidylcholine (lysoPC) (16:0), lysoPC (20:4), lysoPC (22:6), monoglyceride (18:1/0:0/0:0) and sphingomyelin (d18:2/16:0).

In another aspect, the present disclosure provides a kit for diagnosis of acute coronary syndrome, which further includes an in-vivo level detector of one or more metabolite selected from a group consisting of fatty acid (16:1), fatty acid (18:0), fatty acid (18:1), fatty acid (18:2), fatty acid (22:6), lysoPC (18:0) and lysoPC (20:3).

In another aspect, the present disclosure provides a method for providing information for diagnosis of acute coronary syndrome, including: a step of measuring the level of one or more metabolite selected from a group consisting of tryptophan, homoserine, phosphatidylcholine (PC) (34:2), PC (34:3), lysophosphatidylcholine (lysoPC) (16:0), lysoPC (20:4), lysoPC (22:6), monoglyceride (18:1/0:0/0:0) and sphingomyelin (d18:2/16:0) from a biological sample;

and a step of comparing the measured level of the metabolite with the level of a normal control group.

In another aspect, the present disclosure provides a method for providing information for diagnosis of acute coronary syndrome, wherein the step of measuring the level of the metabolite further includes measuring the level of one or more metabolite selected from a group consisting of fatty acid (16:1), fatty acid (18:0), fatty acid (18:1), fatty acid (18:2), fatty acid (22:6), lysoPC (18:0) and lysoPC (20:3) from the biological sample.

The present disclosure allows for easy detection and analysis because metabolites such as amino acids or lipids are used as biomarkers. In addition, since the metabolites according to the present disclosure show specifically increased or decreased concentration in vivo, e.g., in blood, in a subject with coronary disease such as myocardial infarction or angina, the coronary disease can be diagnosed simply and accurately by comparing and analyzing the in-vivo level.

Furthermore, unlike the existing diagnostic method using a single biomarker, the present disclosure allows for more accurate diagnosis with superior sensitivity, specificity and accuracy as compared to the existing method by monitoring the change in in-vivo level of 16 different metabolites having different metabolic pathways through multivariate analysis and applying the same to a single diagnostic platform.

Through this, the present disclosure can diagnose not only acute myocardial infarction but also unstable angina which occurs prior to the myocardial infarction at different stages, whereas the existing biomarker can diagnose only the myocardial infarction based on the necrosis of heart muscle cells. Therefore, the present disclosure is useful for early diagnosis of myocardial infarction at different stages even prior to the onset of the myocardial infarction. Accordingly, by using the multi-metabolite marker diagnostic platform according to the present disclosure, the prognosis of acute myocardial infarction and unstable angina can be predicted and diagnosed via a simple test and even the therapeutic effect and the possibility of disease prevention can be determined.

BRIEF DESCRIPTION OF THE DRAWINGS

FIG. 2 shows a curve for diagnosing acute myocardial infarction in a normal control group, FIG. 3 shows a curve for diagnosing unstable angina in a normal control group, and FIG. 4 shows a curve for diagnosing unstable angina and acute myocardial infarction patient groups. The AUC (the area under the ROC curve) value in each curve is a measure of accuracy. Sensitivity, specificity and accuracy for each case were calculated and presented.

FIG. 5 shows a curve for diagnosing acute myocardial infarction in a normal control group, FIG. 6 shows a curve for diagnosing unstable angina in a normal control group, and FIG. 7 shows a curve for diagnosing unstable angina and acute myocardial infarction patient groups. The AUC value in each curve is a measure of accuracy. Sensitivity, specificity and accuracy for each case were calculated and presented.

DETAILED DESCRIPTION

Figure 1:
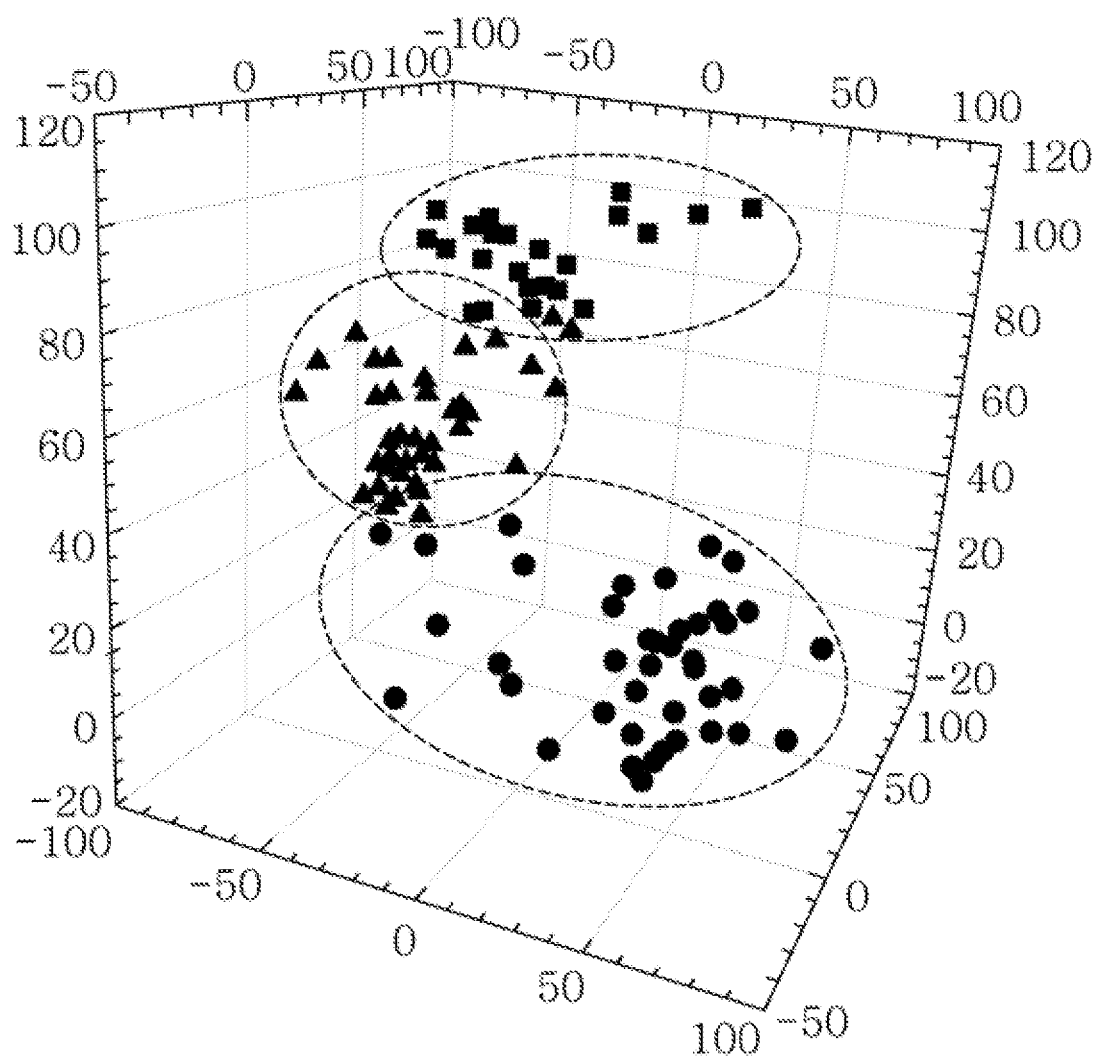
FIG. 1 shows a result of multivariate analysis by partial least squares discriminant analysis (PLS-DA) based on the analysis of metabolites from the serum of a normal control group, a myocardial infarction patient group and an unstable angina patient group. Clusters from the groups are represented as 3-dimensional score plots.

As used herein, the term "level" refers to a level of a metabolite in vivo or in a biological sample. The term is used in the broadest sense, including an objective amount such as concentration, mass, etc. of a metabolite included in blood or other biological samples as well as a relative amount with respect to other substances.

Hereinafter, the present disclosure is described in detail.

In an aspect, the present disclosure provides a biomarker for diagnosis of acute coronary syndrome, containing one or more metabolite selected from a group consisting of tryptophan, homoserine, fatty acid (16:1), fatty acid (18:0), fatty acid (18:1), fatty acid (18:2), fatty acid (22:6), phosphatidylcholine (PC) (34:2), PC (34:3), lysophosphatidylcholine (lysoPC) (16:0), lysoPC (18:0), lysoPC (20:3), lysoPC (20:4), lysoPC (22:6), monoglyceride (18:1/0:0/0:0) and sphingomyelin (d18:2/16:0). The metabolites according to the present disclosure allow for diagnosis of acute coronary syndrome as well as unstable angina and asymptomatic unstable angina as risk factors of acute coronary syndrome stage by stage. In addition, the metabolites according to the present disclosure can be used to diagnose any cardiovascular disease without being limited to the above diseases.

In this respect, the present disclosure provides an acute coronary syndrome diagnostic platform, including a multi in-vivo level detector of one or more metabolite selected from a group consisting of tryptophan, homoserine, phosphatidylcholine (PC) (34:2), PC (34:3), lysoPC (16:0), lysoPC (20:4), lysoPC (22:6), monoglyceride (18:1/0:0/0:0) and sphingomyelin (d18:2/16:0). The platform may include a kit for diagnosis of acute coronary syndrome.

In an exemplary embodiment, the kit for diagnosis may further include an in-vivo level detector of one or more metabolite selected from a group consisting of fatty acid (16:1), fatty acid (18:0), fatty acid (18:1), fatty acid (18:2), fatty acid (22:6), lysoPC (18:0) and lysoPC (20:3). More specifically, the kit for diagnosis may include an in-vivo level detector measuring the in-vivo level of 3 or more, 6 or more, 10 or more, 12 or more or 14 or more metabolites selected from a group consisting of tryptophan, homoserine, fatty acid (16:1), fatty acid (18:0), fatty acid (18:1), fatty acid (18:2), fatty acid (22:6), phosphatidylcholine (PC) (34:2), PC (34:3), lysoPC (16:0), lysoPC (18:0), lysoPC (20:3), lysoPC (20:4), lysoPC (22:6), monoglyceride (18:1/0:0/0:0) and sphingomyelin (d18:2/16:0). Alternatively, it may include a multi-metabolite detector measuring the in-vivo level of the 16 metabolites.

Among the above-described metabolites, tryptophan and homoserine are amino acids and are present mainly in L-form in vivo. In particular, tryptophan is one of essential amino acids and plays an important role in metabolism.

Among the above-described metabolites, PC (34:3), lysoPC (16:0), lysoPC (18:0), lysoPC (20:3), lysoPC (20:4) and lysoPC (22:6) are phospholipid metabolites called phosphatidylcholines (PC) or lysoPC which are involved in lipid metabolic pathways in cell membranes, blood, etc. As can be seen from Chemical Formula 1, PC is a compound in which two fatty acids R' and R" are bound to phosphocholine. LysoPC, which is an abbreviation for lysophosphatidylcholine, has a structure in which only one fatty acid (R' in Chemical Formula 1) is bound to PC as one fatty acid is removed therefrom. The PC (34:3), lysoPC (16:0), lysoPC (18:0), lysoPC (20:3), lysoPC (20:4) and lysoPC (22:6) mean, respectively, a PC or a lysoPC wherein the numbers of carbon atoms and double bonds (carbon atoms:double bonds) in the carbon chain are 34:3, 16:0, 18:0, 20:3, 20:4 and 22:6. The change in in-vivo level in acute coronary syndrome patients is different depending on the numbers.

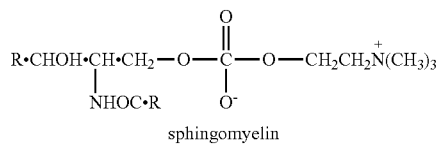

Chemical Formula 3 sphingomyelin

In an exemplary embodiment, the acute coronary syndrome may include one or more of acute myocardial infarction and unstable angina occurring prior to the onset of acute myocardial infarction. Specifically, the 16 metabolites may

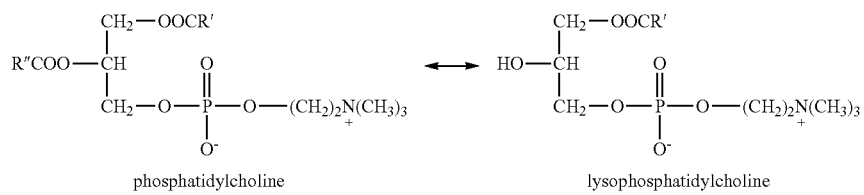

Chemical Formula 1 phosphatidylcholine            lysophosphatidylcholine

A fatty acid (FA) is a monovalent carboxylic acid of a hydrocarbon chain having one carboxyl group (—COOH). Fatty acids are degraded or synthesized in vivo via the fatty acid cycle. Alike the lysoPC, it is also represented by the numbers of carbon atoms and double bonds (carbon atoms: double bonds) in the carbon chain. The fatty acid (16:1), fatty acid (18:0), fatty acid (18:1), fatty acid (18:2) and fatty acid (22:6) mean, respectively, a fatty acid wherein the numbers of carbon atoms and double bonds (carbon atoms: double bonds) in the carbon chain are 16:1, 18:0, 18:1, 18:2 and 22:6. They are called, respectively, palmitelaidic acid, stearic acid, oleic acid, linoleic acid and docosahexaenoic acid.

Monoglyceride (MG) is a metabolite derived from glycerol, in which one fatty acid $R_1$ is bound to glycerol, as seen from Chemical Formula 2.

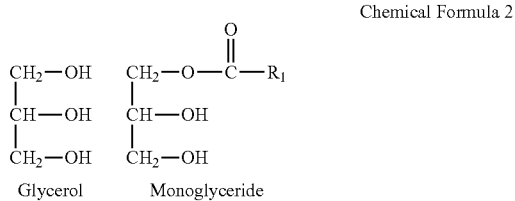

Chemical Formula 2

Glycerol    Monoglyceride

Sphingomyelin (SM) is a kind of a phospholipid metabolite. When compared with the PC-based metabolite, it differs in that an amine group is added and is similar in that there are two fatty acids R' and R", as seen from Chemical Formula 3.

show different change in in-vivo level in acute myocardial infarction patients and unstable angina patients as compared to the normal control group. In addition, the 16 metabolites may also exhibit different change in in-vivo level in the same subject.

In an exemplary embodiment, the in-vivo level detector of the metabolites may include a material, a detecting device, etc. capable of detecting one or more of the 16 metabolites from, for example, blood, serum, blood plasma, urine, etc. Any means capable of measuring or detecting the in-vivo level of the metabolites, e.g., a mass analyzer, a nuclear magnetic resonance (NMR) spectrometer, a photodiode array (PDA), etc., may be used without limitation.

For example, in an exemplary embodiment, the in-vivo level detector of the metabolite may include a composition for diagnosis of acute coronary syndrome containing a material for detecting one or more metabolite selected from a group consisting of tryptophan, homoserine, phosphatidylcholine (PC) (34:2), PC (34:3), lysophosphatidylcholine (lysoPC) (16:0), lysoPC (20:4), lysoPC (22:6), monoglyceride (18:1/0:0/0:0) and sphingomyelin (d18:2/16:0) as an active ingredient.

In an exemplary embodiment, the in-vivo level detector of the metabolite may include a composition for diagnosis of acute coronary syndrome containing a material for detecting one or more metabolite selected from a group consisting of fatty acid (16:1), fatty acid (18:0), fatty acid (18:1), fatty acid (18:2), fatty acid (22:6), lysoPC (18:0) and lysoPC (20:3) as an active ingredient.

In another exemplary embodiment of the present disclosure, the composition for diagnosis may contain a material detecting 3 or more, 6 or more, 10 or more, 12 or more or 14 or more multiple metabolites selected from a group consisting of tryptophan, homoserine, fatty acid (16:1), fatty acid (18:0), fatty acid (18:1), fatty acid (18:2), fatty acid (22:6), phosphatidylcholine (PC) (34:2), PC (34:3), lysoPC (16:0), lysoPC (18:0), lysoPC (20:3), lysoPC (20:4), lysoPC (22:6), monoglyceride (18:1/0:0/0:0) and sphingomyelin (d18:2/16:0) as an active ingredient. More specifically, the composition for diagnosis may contain a material detecting the 16 metabolites as an active ingredient.

In an exemplary embodiment of the present disclosure, the acute coronary syndrome diagnosed using the composition for diagnosis may include one or more of acute myocardial infarction and unstable angina occurring prior to the onset of acute myocardial infarction. However, any cardiovascular disease may be included without being limited thereto. The composition for diagnosis containing the material detecting all the multiple metabolites as an active ingredient may diagnose acute myocardial infarction and unstable angina occurring prior to the onset of acute myocardial infarction from among the acute coronary syndrome more accurately than the composition containing a material detecting only one metabolite.

In an exemplary embodiment, the kit for diagnosis further of the present disclosure may further include an instruction for an acute coronary syndrome diagnosis method. Since the acute coronary syndrome may include one or more of myocardial infarction and unstable angina, the instruction may also include a method for diagnosing one or more of myocardial infarction and unstable angina. In addition, since the kit for diagnosis according to the present disclosure may be used to diagnose any cardiovascular disease without being limited to the above-described diseases, the instruction may further include an instruction for a diagnosis method of ischemic heart disease, coronary artery disease, angina, myocardial infarction, atherosclerosis (arteriosclerosis), etc.

In an exemplary embodiment, the acute coronary syndrome diagnosis method may include diagnosing as acute coronary syndrome when the in-vivo level of one or more of tryptophan, PC (34:3), lysoPC (16:0) and lysoPC (18:0) from among the metabolites measured by the in-vivo level detector is lower as compared to a normal control group or when the in-vivo level of one or more of homoserine, fatty acid (16:1), fatty acid (18:0), fatty acid (18:1), fatty acid (18:2), fatty acid (22:6), PC (34:2), lysoPC (20:3), lysoPC (20:4), lysoPC (22:6), monoglyceride (18:1/0:0/0:0) and sphingomyelin (d18:2/16:0) is higher as compared to the normal control group.

The metabolites according to the present disclosure have been selected through analysis of serum from a normal control group and acute coronary syndrome patient groups, specifically an acute myocardial infarction patient group and an unstable angina patient group, and interpretation of data via a metabolomic approach. Since metabolomics analyzes the composition and level of small-molecule metabolites in vivo due to genetic difference and change in physiological or environmental conditions to understand the cause of various physiological changes in vivo, the change in metabolic pathways due to coronary disease occurring in a subject can be analyzed effectively by selecting the metabolites based on metabolomics.

In an exemplary embodiment of the present disclosure, kit for diagnosis may further include a multivariate analysis system analyzing the in-vivo level of the metabolites measured by the metabolite detector.

The multivariate analysis system refers to a statistical system analyzing the specific change in in-vivo level of two or more among the 16 metabolites due to the onset of acute coronary syndrome or the likelihood of the onset. The multivariate analysis may be conducted by analyzing the difference in the in-vivo level of the metabolites relative to a normal control group of healthy people without the acute coronary syndrome or other diseases. However, it is not particularly limited as long as the onset of the acute coronary syndrome can be detected based on the change in the in-vivo level of the 16 metabolites. The multivariate analysis is contrasted with univariate analysis wherein only one metabolite or biomarker is analyzed and any statistical system for analyzing the change in the in-vivo level of two or more of the 16 metabolites at the same time may be used. Specifically, the multivariate analysis may be conducted using a statistical system capable of analyzing the change in the in-vivo level of the 16 metabolites. More specifically, the multivariate analysis system may be a multivariate ROC curve model optimized for the 16 metabolites through repeated evaluation by Monte Carlo cross validation.

When acute coronary syndrome is diagnosed by the general univariate analysis method using a single biomarker, it is difficult to make an accurate diagnosis at different stages of the acute coronary syndrome because of insufficient sensitivity, specificity and accuracy. In contrast, when the multivariate analysis system according to the present disclosure is used to analyze the in-vivo level of the metabolites measured by the metabolite detector, both acute myocardial infarction and unstable angina can be detected and diagnosed at different stages of the disease due to good sensitivity, specificity and accuracy.

In another aspect, the present disclosure provides a method for providing information for diagnosis of acute coronary syndrome, including: a step of measuring the level of one or more metabolite selected from a group consisting of tryptophan, homoserine, phosphatidylcholine (PC) (34:2), PC (34:3), lysophosphatidylcholine (lysoPC) (16:0), lysoPC (20:4), lysoPC (22:6), monoglyceride (18:1/0:0/0:0) and sphingomyelin (d18:2/16:0) from a biological sample; and a step of comparing the measured level of the metabolite with the level of a normal control group. The step of measuring the level of the metabolite may further include measuring the level of one or more metabolite selected from a group consisting of fatty acid (16:1), fatty acid (18:0), fatty acid (18:1), fatty acid (18:2), fatty acid (22:6), lysoPC (18:0) and lysoPC (20:3) from the biological sample.

More specifically, the step of measuring the level of the metabolite may include a multi-metabolite measuring step of measuring the level of 3 or more, 6 or more, 10 or more, 12 or more or 14 or more metabolites selected from a group consisting of tryptophan, homoserine, fatty acid (16:1), fatty acid (18:0), fatty acid (18:1), fatty acid (18:2), fatty acid (22:6), phosphatidylcholine (PC) (34:2), PC (34:3), lysoPC (16:0), lysoPC (18:0), lysoPC (20:3), lysoPC (20:4), lysoPC (22:6), monoglyceride (18:1/0:0/0:0) and sphingomyelin (d18:2/16:0). More specifically, the step of measuring the level of the metabolite may include a step of measuring the level of the 16 metabolites.

In an exemplary embodiment, the biological sample in the step of measuring the level of the metabolite may be a sample taken from human or an animal excluding human. More specifically, the biological sample may include blood, serum, blood plasma, urine, etc. taken from human or an animal excluding human. The level of the metabolite may be, for example, an objective amount such as concentration, mass, etc. of the metabolite included in blood as well as a relative amount with respect to other substances. In addition, the method of measuring the level may include taking blood from a subject, analyzing the same, and then analyzing the content or concentration of the metabolite. The sample may be taken from, in addition to the blood, tissue, urine, etc., although not being limited thereto.

In an exemplary embodiment, the method for providing information for diagnosis of acute coronary syndrome may further include, after the step of comparing the measured level of the metabolite with the level of a normal control group, a step of diagnosing as acute coronary syndrome when the in-vivo level of one or more of tryptophan, PC (34:3), lysoPC (16:0) and lysoPC (18:0) from among the measured metabolites is lower as compared to a normal control group. Also, it may further include, after the step of comparing the measured level of the metabolite with the level of a normal control group, a step of diagnosing as acute coronary syndrome when the in-vivo level of one or more of homoserine, fatty acid (16:1), fatty acid (18:0), fatty acid (18:1), fatty acid (18:2), fatty acid (22:6), PC (34:2), lysoPC (20:3), lysoPC (20:4), lysoPC (22:6), monoglyceride (18:1/0:0/0:0) and sphingomyelin (d18:2/16:0) is higher as compared to the normal control group. Alternatively, it may further include a step of comparing the blood level of the 16 metabolites at the same time. In an exemplary embodiment of the present disclosure, the normal control group means a group of healthy people without special diseases.

In an exemplary embodiment, the method for providing information for diagnosis of acute coronary syndrome may further include a step of conducting multivariate analysis of the level of the metabolites measured in the multi-metabolite measuring step. In an exemplary embodiment of the present disclosure, information for diagnosing acute myocardial infarction from among the acute coronary syndrome and unstable angina occurring prior to the onset of acute myocardial infarction may be provided through this step.

In another exemplary embodiment of the present disclosure, the composition or kit for diagnosis of acute coronary syndrome according to the present disclosure described above may be used in the method for providing information for diagnosis of acute coronary syndrome.

Hereinafter, the present disclosure will be described in detail through examples. However, the following examples are for illustrative purposes only and it will be apparent to those of ordinary skill in the art that the scope of the present disclosure is not limited by the examples.

Example 1

Experiment was conducted as follows in order to confirm the function of the 16 metabolites according to the present disclosure, tryptophan, homoserine, fatty acid (16:1), fatty acid (18:0), fatty acid (18:1), fatty acid (18:2), fatty acid (22:6), PC (34:2), PC (34:3), lysoPC (16:0), lysoPC (18:0), lysoPC (20:3), lysoPC (20:4), lysoPC (22:6), monoglyceride (18:1/0:0/0:0) and sphingomyelin (d18:2/16:0), as diagnostic biomarkers for diagnosis of acute myocardial infarction at different stages and utilize them for a multi-metabolite platform.

1. Selection of Test Subjects

Healthy people without cardiovascular disease as a normal control group and unstable angina and acute myocardial infarction patients as acute coronary syndrome patient groups were recruited as test participants from Korea University Guro Hospital (Seoul, Korea). The acute coronary syndrome patient groups consisted of 23 unstable angina patients and 42 myocardial infarction patients, and the normal control group consisted of 40 healthy men and women. Age was restricted to 45 years or older for both the patient group and the control group in order to prevent data interpretation error that may occur due to difference in age. The age was restricted to 45 years or older because cardiovascular disease such as myocardial infarction or angina occurs more frequently in middle and old ages than in younger people and shows significant difference at the age of 45 years or older.

2. Preparation of Serum Sample

Venous blood was taken from the patient group and the normal control group and a serum sample was obtained by centrifugation. All the serum samples were stored at −80° C. prior to analysis. The serum sample was pretreated with methanol for deproteination. A specific pretreatment method was as follows. 3 volume equivalents of ice-cold methanol was added to the serum sample thawed to room temperature and mixed completely. After centrifugation, a predetermined amount of supernatant was collected and diluted by adding distilled water of half (½) the volume of the supernatant.

3. Analysis of Metabolite by Ultra Performance Liquid Chromatography-Quadrupole Time-of-Flight Mass Spectrometry (UPLC-QTOF-MS)

The pretreated serum sample of the patient group and the normal control group was analyzed by ultra performance liquid chromatography-quadrupole time-of-flight mass spectrometry (UPLC-QTOF-MS; ACQUITY UPLC system and Synapt G2 MS system, Waters).

The metabolites included in the serum sample were separated according to their retention time while passing through the UPLC system and detected by their mass-to-charge ratio as they pass through the Synapt G2 MS system. Specifically, an ACQUITY BEH $C_{18}$ (2.1×100 mm, 1.7 μm) column was used for the UPLC system and the temperature of the column and an autosampler was kept at 50° C. and 4° C., respectively. As mobile phases, distilled water containing 0.1% formic acid (mobile phase A) and methanol containing 0.1% formic acid (mobile phase B) were used. The two mobile phases were flown at different mixing ratios with time (gradient elution). The injection sequence was randomized to avoid tendency resulting from the injection sequence. The metabolites included in the serum sample were detected by the Synapt G2 system in positive and negative ionization modes and were analyzed in the $MS^E$ mode.

The specific analysis condition of the Synapt G2 system was as follows.

TABLE 1

| Acquisition mode | ESI (+/−) mode |
| --- | --- |
| Capillary voltage | (+) 3.2 kV/(−) 2.5 kV |
| Sample cone voltage | 40 V |
| Source temperature | 120° C. |
| Desolvation temperature | 350° C. |
| Cone gas flow | 100 L/h |
| Desolvation gas flow | 800 L/h |

Specifically, the analysis was made by electrospray ionization (ESI) with the capillary voltage set at (+) 3.2 kV for the positive ionization mode and at (−) 2.5 kV for the negative ionization mode and the cone voltage set at 40 V. Source temperature and desolvation temperature were set at 120° C. and 350° C., respectively, and cone gas flow rate and desolvation gas flow rate were set at 100 L/h and 800 L/h, respectively. Chromatogram and mass spectrum data analysis were obtained from the serum analysis result by ultra performance liquid chromatography-quadrupole time-of-flight mass spectrometry (UPLC-QTOF-MS).

4. Analysis of Metabolites in Serum Samples from Unstable Angina and Myocardial Infarction Patient Groups and Normal Control Group The chromatogram and mass spectrum analysis data obtained from the serum samples of the unstable angina and myocardial infarction patient groups and the normal control group were deconvoluted using MassLynx™ (mass spectrometry software, Waters) and MarkerLynx™ (Waters)

programs to obtain data for the detected metabolite marker candidates. The peak area of each marker candidate was corrected for the total chromatogram peak area for minimization of errors between sample data and for normalization. The normalized marker data were subjected to multivariate analysis using the partial least squares discriminant analysis (PLS-DA) method. FIG. 1 shows a 3-dimensional representation of the multivariate analysis result. The three distinct clusters in the score plot of FIG. 1 show that the three groups exhibit distinct difference in marker profiles.

Then, among the marker candidates showing difference between the groups in the statistical analysis, the metabolite biomarkers exhibiting the highest statistically significant difference were selected and their difference in the normal group and the patient group or their change at different stages patient group was analyzed. That is to say, from among the selected candidates, the biomarkers related with myocardial infarction and unstable angina were compared and identified by searching databases such as the Human Metabolome Database (HMDB) and the METLIN Metabolomics Database.

The mean of the level of the 16 biomarkers which showed statistically significant difference between normal control group and the patient groups is shown in Table 2. The significant difference of the 16 biomarkers was tested by the Kruskal-Wallis test and the Student's t-test. The p-values of the 12 biomarkers that showed significant difference are shown in Table 3. The mean values given in the tables are normalized peak area values.

TABLE 2

| Material name | Normal control group Mean | SD | Unstable angina patient group Mean | SD | Acute myocardial infarction patient group Mean | SD | Change |
|---|---|---|---|---|---|---|---|
| L-Tryptophan | 19.1 | 9.5 | 17.4 | 10.9 | 5.0 | 5.4 | Decreased |
| L-Homoserine | 5.7 | 3.3 | 5.0 | 4.0 | 14.9 | 11.5 | Increased |
| FA (16:1) (palmitelaidic acid) | 67.9 | 35.8 | 90.7 | 57.9 | 120.7 | 54.3 | Increased |
| FA (18:0) (stearic acid) | 45.9 | 10.2 | 54.6 | 18.2 | 62.3 | 12.2 | Increased |
| FA (18:1) (oleic acid) | 236.9 | 86.3 | 308.3 | 173.8 | 478.4 | 212.2 | Increased |
| FA (18:2) (linoleic acid) | 223.7 | 63.4 | 262.3 | 93.2 | 343.7 | 105.1 | Increased |
| FA (22:6) (docosahexaenoic acid) | 168.4 | 62.0 | 209.1 | 122.2 | 259.4 | 98.1 | Increased |
| PC (34:2) | 204.5 | 49.1 | 208.1 | 34.4 | 210.1 | 32.6 | Increased |
| PC (34:3) | 10.6 | 4.6 | 8.5 | 5.0 | 7.9 | 4.8 | Decreased |
| LPC (16:0) | 529.7 | 82.1 | 480.4 | 96.9 | 449.6 | 128.9 | Decreased |
| LPC (18:0) | 184.8 | 45.3 | 164.5 | 34.9 | 128.3 | 64.0 | Decreased |
| LPC (20:3) | 4.3 | 1.8 | 5.9 | 3.0 | 8.4 | 5.2 | Increased |
| LPC (20:4) | 14.6 | 5.2 | 20.6 | 12.6 | 27.2 | 21.1 | Increased |
| LPC (22:6) | 8.6 | 3.6 | 27.8 | 38.9 | 37.3 | 34.0 | Increased |
| MG (18:1/0:0/0:0) | 27.1 | 35.4 | 51.1 | 85.2 | 134.1 | 109.2 | Increased |
| SM (d18:2/16:0) | 7.0 | 2.7 | 9.7 | 4.9 | 11.8 | 4.3 | Increased |

TABLE 3

| | | Student's t-test | | |
|---|---|---|---|---|
| Material name | Kruskal-Wallis test | Normal control group vs. acute myocardial infarction group | Normal control group vs. unstable angina group | Acute myocardial infarction group vs. unstable angina group |
| L-Tryptophan | <0.001 | <0.001 | 0.526 | <0.001 |
| L-Homoserine | <0.001 | <0.001 | 0.508 | <0.001 |
| FA (18:0) (stearic acid) | <0.001 | <0.001 | 0.073 | 0.047 |
| FA (18:1) (oleic acid) | <0.001 | <0.001 | 0.076 | 0.002 |
| FA (18:2) (linoleic acid) | <0.001 | <0.001 | 0.087 | 0.003 |
| FA (22:6) (docosahexaenoic acid) | <0.001 | <0.001 | 0.147 | 0.075 |
| PC (34:3) | 0.022 | 0.012 | 0.086 | 0.681 |
| LPC (16:0) | <0.001 | 0.001 | 0.031 | <0.001 |
| LPC (18:0) | <0.001 | <0.001 | 0.068 | 0.005 |
| LPC (20:3) | <0.001 | <0.001 | 0.028 | 0.017 |
| LPC (20:4) | 0.002 | <0.001 | 0.038 | 0.119 |
| MG (18:1/0:0/0:0) | <0.001 | <0.001 | 0.208 | 0.002 |

As seen from Table 2, the metabolites increased or decreased in the unstable angina patient group and the myocardial infarction patient group as compared to the normal control group were identified. They were mostly amino acids, phospholipids and fatty acids. PC, lysoPC and sphingomyelin (SM) were included among the phospholipids. As for the lysoPC, unsaturated lysoPC such as lysoPC (20:3), lysoPC (20:4) and lysoPC (22:6) was increased in the patient groups as compared to the normal control group, whereas saturated lysoPC such as lysoPC (16:0) and lysoPC (18:0) was decreased. As for the PC, PC (34:2) was increased and PC (34:3) was decreased. And, fatty acid-based metabolites such as monoglyceride (MG) (18:1/0:0/0:0) and sphingomyelin (SM) (d18:2/16:0) were increased.

The 12 biomarkers listed in Table 3 are those which showed significant difference in the Kruskal-Wallis test from among the 16 metabolites described in Table 2. The difference at different stages of a particular disease was assessed by the Student's t-test whereby the difference between groups is assessed via a nonparametric test unlike the Kruskal-Wallis test. Whereas all the 12 biomarkers showed significant difference in the Kruskal-Wallis test, some of them did not show significant p-values (<0.05) at different stages of the diseases.

Figure 2:
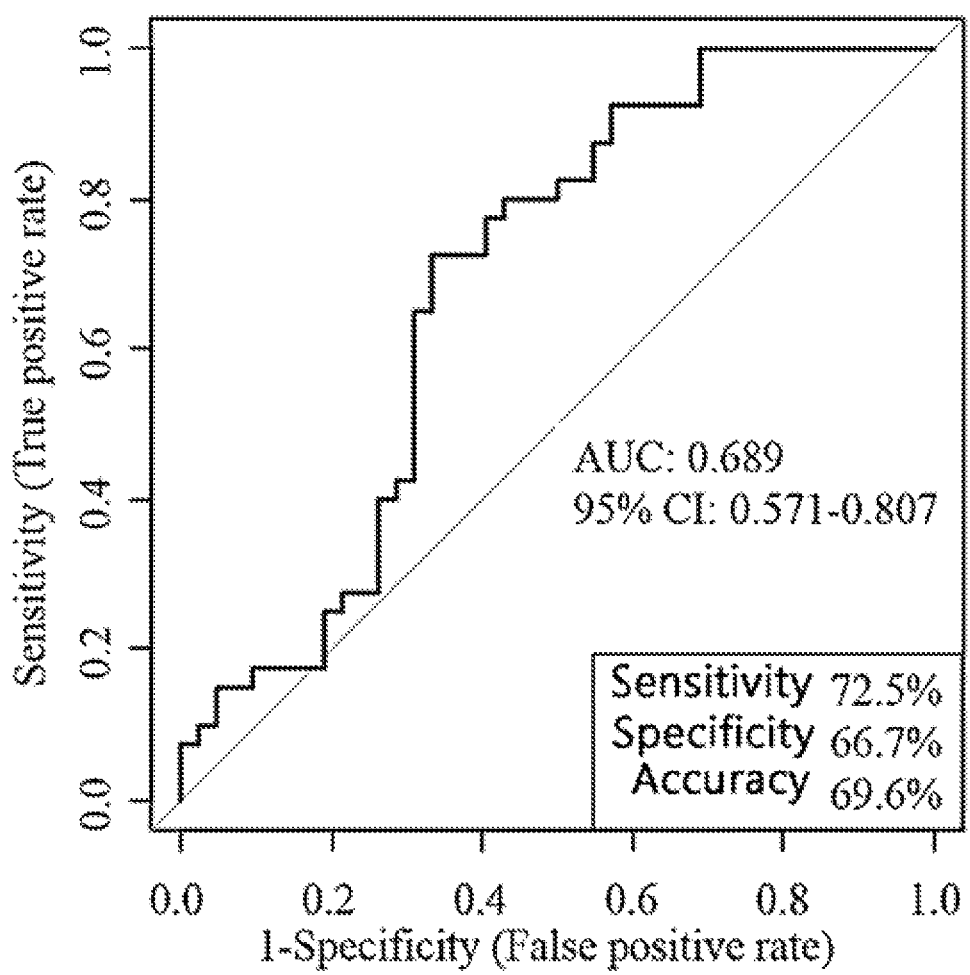
FIGS. 2-4 show univariate receiver operating characteristic (ROC) curves for diagnosing a normal control group and unstable angina and myocardial infarction patient groups utilizing the relative blood level data of lysoPC (16:0) in Example 1.
Figure 3:
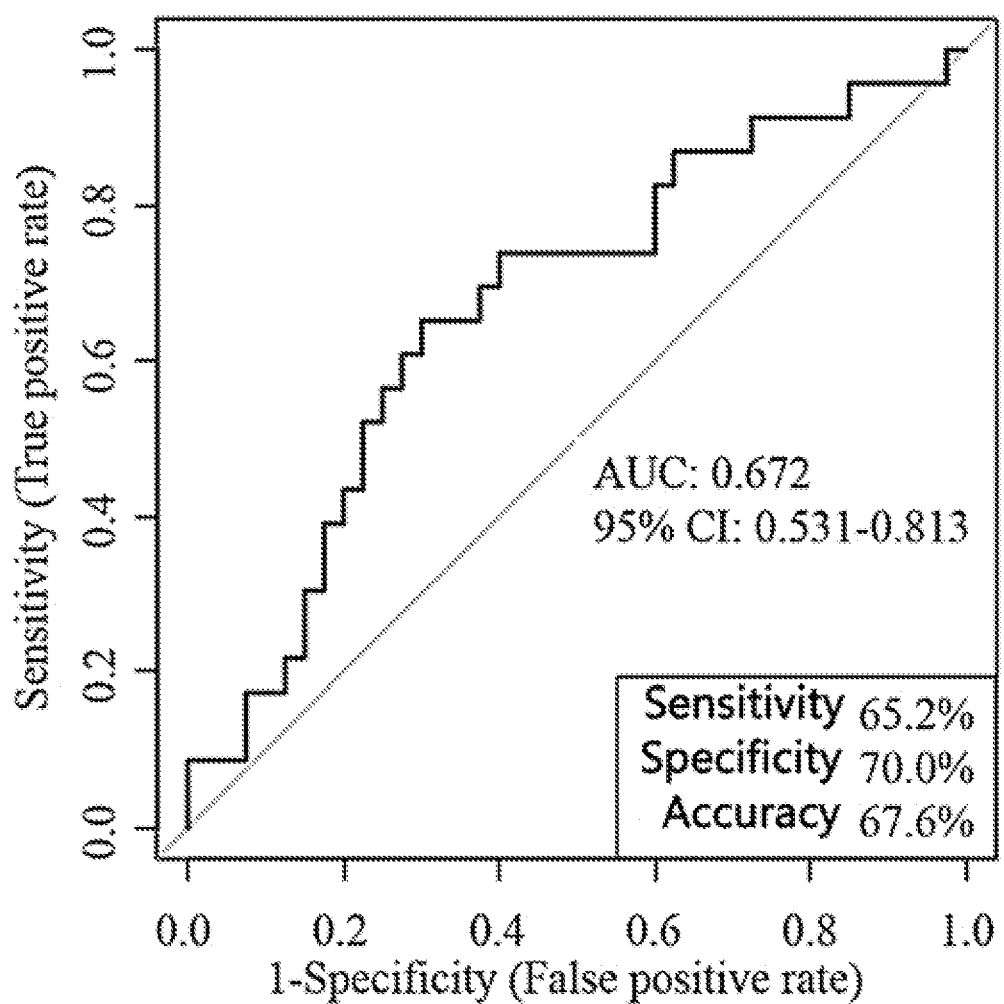
Figure 4:
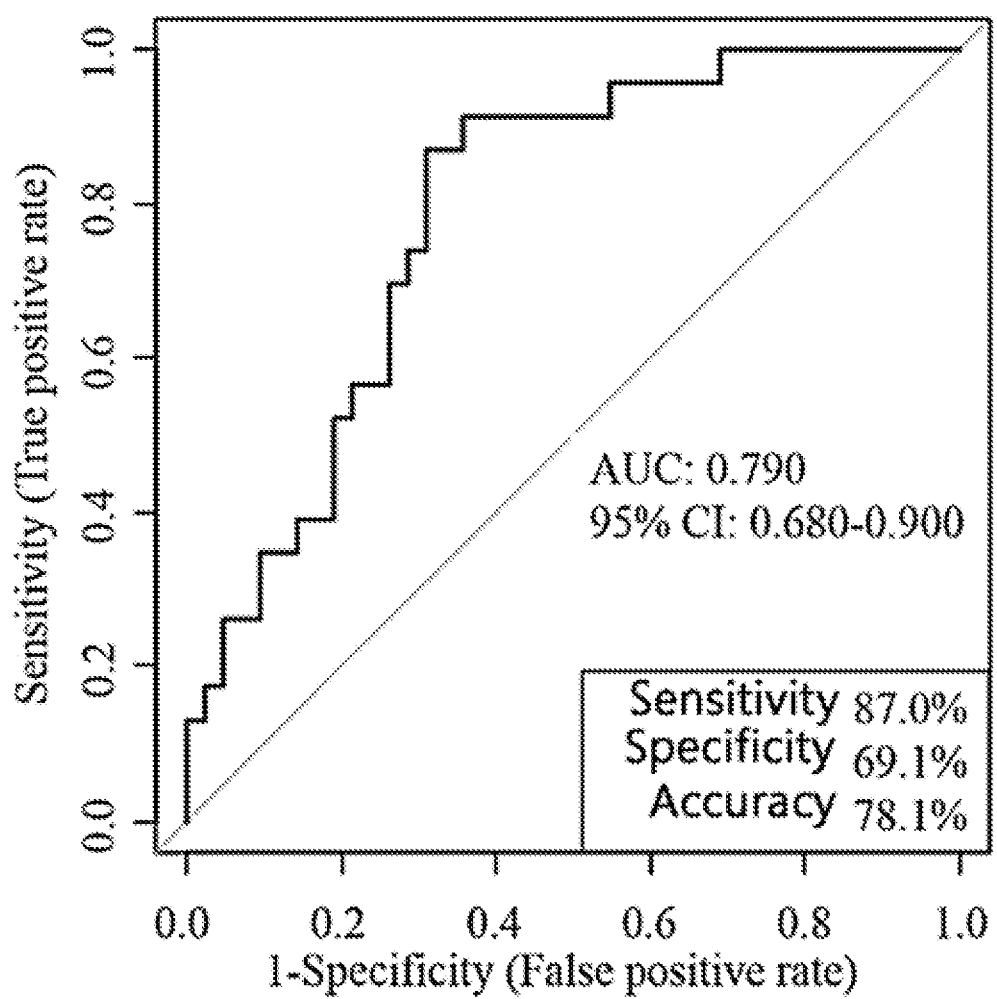

Receiver operating characteristic (ROC) analysis was conducted to assess the accuracy of the change in the level of each biomarker as a biomarker for diagnosing acute myocardial infarction and unstable angina at different stages. First, univariate ROC curves were constructed for the single biomarker lysoPC (16:0) which showed significant difference for the diseases in both the Kruskal-Wallis test and the Student's t-test and sensitivity, specificity and accuracy were calculated therefrom. The result is shown in FIGS. 2-4. FIG. 2 shows a result of comparing the normal control group with the acute myocardial infarction patient group, FIG. 3 shows a result of comparing the normal control group with the unstable angina patient group, and FIG. 4 shows a result of comparing the unstable angina patient group with the acute myocardial infarction patient group.

Figure 5:
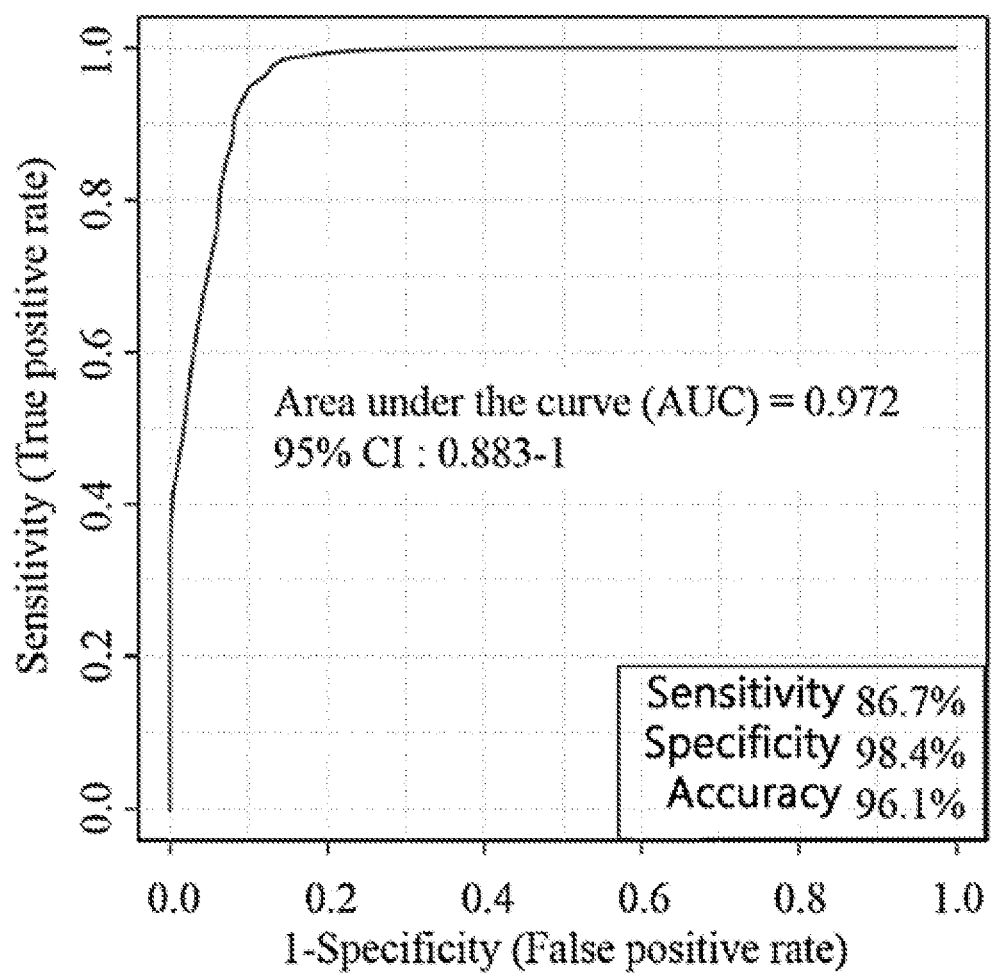
FIGS. 5-7 show multivariate ROC curves obtained using 16 multiple metabolites in Example 1. A multivariate ROC model for diagnosis based on comparison of relative blood level in a normal control group and unstable angina and myocardial infarction patient groups was optimized.
Figure 6:
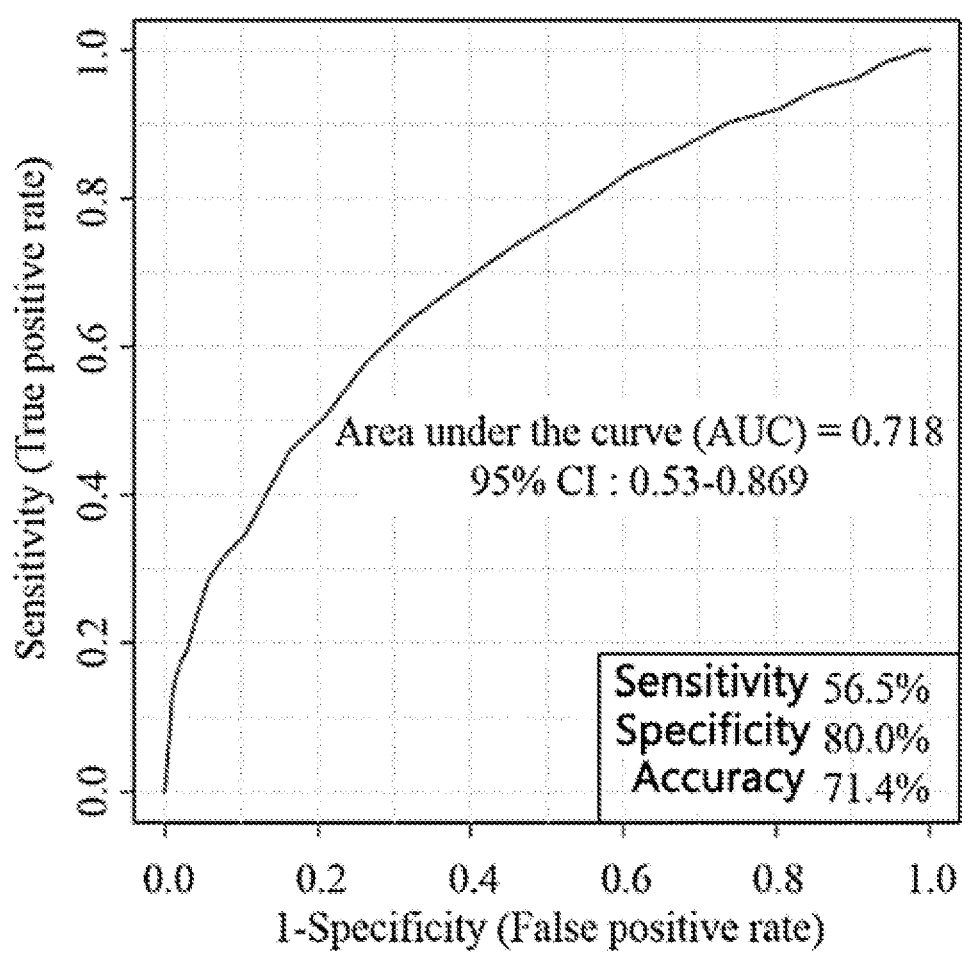
Figure 7:
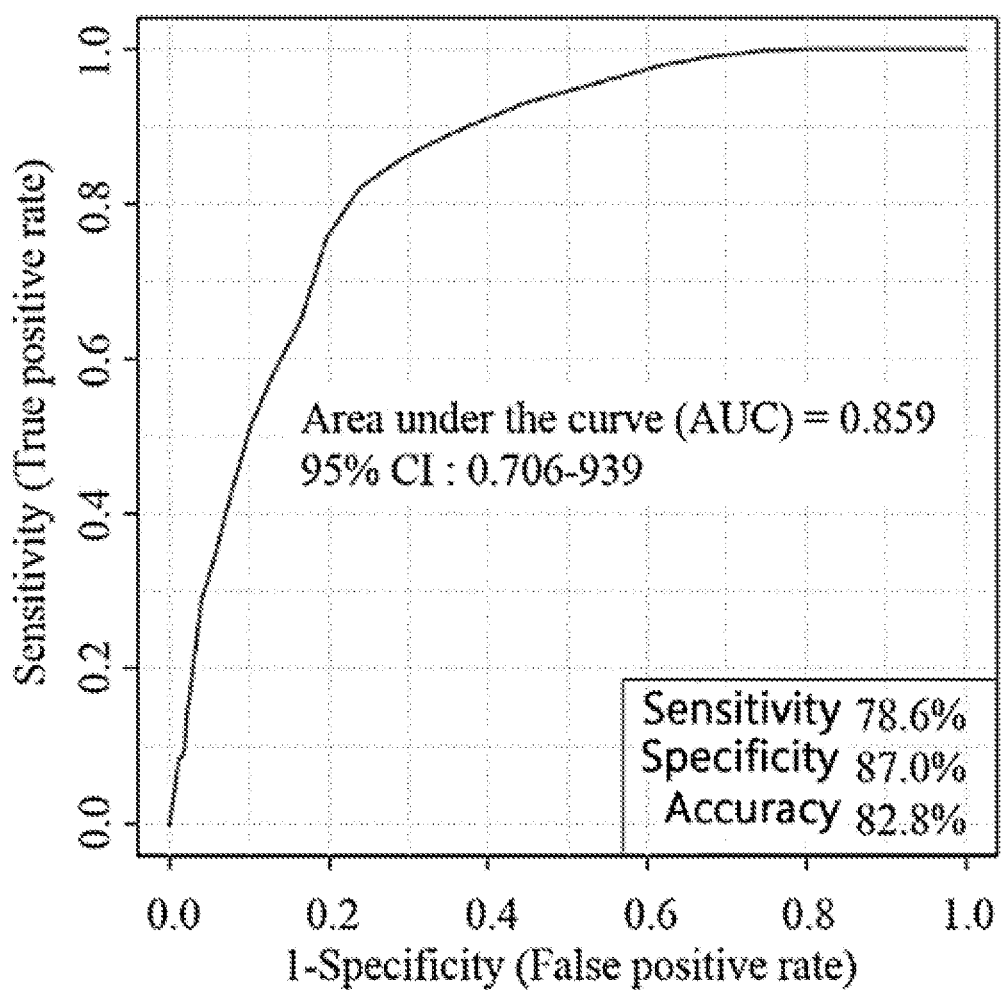

Since sufficient sensitivity, specificity and accuracy cannot be ensured only with the single biomarker as shown in FIGS. 2-4, a multivariate ROC curve model was constructed for the 16 multiple metabolites according to the present disclosure and sensitivity, specificity and accuracy were calculated therefrom. The result is shown in FIGS. 5-7. FIG. 5 shows a result of comparing the normal control group with the acute myocardial infarction patient group, FIG. 6 shows a result of comparing the normal control group with the unstable angina patient group, and FIG. 7 shows a result of comparing the unstable angina patient group with the acute myocardial infarction patient group. The multivariate ROC curve model was optimized for the 16 metabolites through 50 times of repeated evaluation by Monte Carlo cross validation.

From FIGS. 2-4 and FIGS. 5-7, it can be seen that the analysis result from the multivariate ROC curve model using the multiple metabolites shows about 3.8-23.1% increased accuracy as compared to that from the univariate ROC curve using a single biomarker. This suggests that a multivariate analysis system using the 16 multiple metabolites may be utilized as a multi-biomarker diagnostic platform. The diagnostic platform may be utilized not only to diagnose acute myocardial infarction but also to differentiate unstable angina from acute myocardial infarction.

Example 2

To reconfirm the result of Example 1, analysis was conducted for other test participants. The test participants were healthy people without cardiovascular disease as a normal control group and unstable angina and acute myocardial infarction patients as patient groups recruited from Korea University Guro Hospital (Seoul, Korea). The patient groups consisted of 23 unstable angina patients and 15 myocardial infarction patients, and the normal control group consisted of 61 healthy men and women.

The analysis condition and the data processing method were the same as in Example 1.

Figure 8:
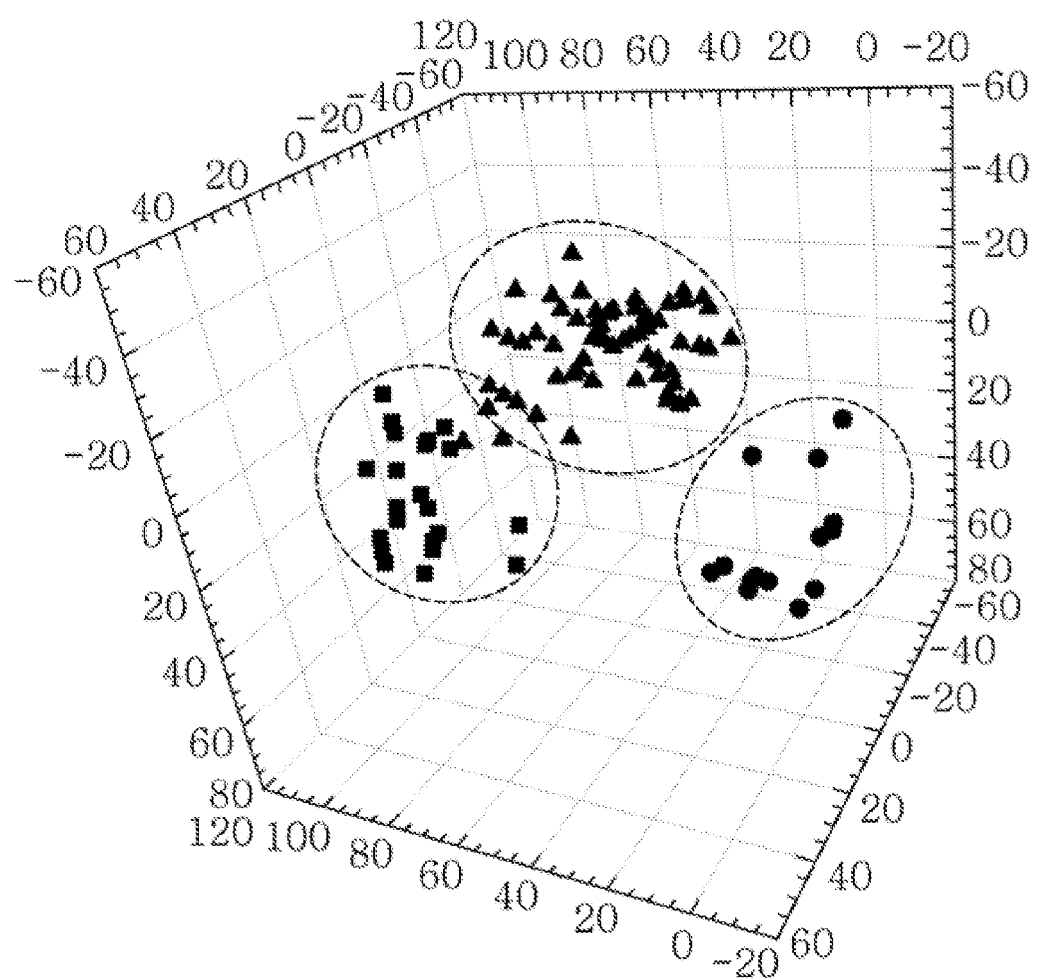
FIG. 8 shows a result of reconfirming the result of FIG. 1 in different test groups in Example 2.

From the 3-dimensionally represented PLS-DA score plot (FIG. 8), it can be seen that the three groups exhibit distinct difference in markers because three distinct clusters were formed.

16 metabolites were selected and the change in the level of the metabolites in the normal control group, the unstable angina patient group and the acute myocardial infarction patient group is shown in Table 4. And, the result of the Kruskal-Wallis test and the Student's t-test is shown in Table 5.

TABLE 4

| Material name | Normal control group Mean | Normal control group SD | Unstable angina patient group Mean | Unstable angina patient group SD | Acute myocardial infarction patient group Mean | Acute myocardial infarction patient group SD | Change |
|---|---|---|---|---|---|---|---|
| L-Tryptophan | 22.4 | 5.1 | 19.5 | 5.8 | 16.5 | 8.0 | Decreased |
| L-Homoserine | 5.0 | 1.1 | 5.5 | 1.4 | 6.4 | 2.4 | Increased |
| FA (16:1) (palmitelaidic acid) | 12.9 | 10.1 | 14.3 | 11.1 | 24.7 | 15.7 | Increased |
| FA (18:0) (stearic acid) | 6.1 | 2.2 | 12.4 | 3.9 | 15.5 | 5.6 | Increased |
| FA (18:1) (oleic acid) | 98.7 | 44.6 | 129.3 | 69.3 | 216.8 | 119.8 | Increased |
| FA (18:2) (linoleic acid) | 88.5 | 32.3 | 106.6 | 67.7 | 165.0 | 59.1 | Increased |
| FA (22:6) (docosahexaenoic acid) | 74.8 | 35.6 | 71.5 | 21.7 | 156.8 | 85.5 | Increased |

TABLE 4-continued

| Material name | Normal control group Mean | Normal control group SD | Unstable angina patient group Mean | Unstable angina patient group SD | Acute myocardial infarction patient group Mean | Acute myocardial infarction patient group SD | Change |
|---|---|---|---|---|---|---|---|
| PC (34:2) | 159.1 | 34.9 | 166.8 | 25.6 | 187.8 | 33.1 | Increased |
| PC (34:3) | 16.4 | 7.4 | 15.3 | 4.9 | 14.5 | 5.4 | Decreased |
| LPC (16:0) | 314.8 | 51.0 | 283.8 | 42.3 | 230.8 | 62.4 | Decreased |
| LPC (18:0) | 95.6 | 26.0 | 82.1 | 22.7 | 61.7 | 25.6 | Decreased |
| LPC (20:3) | 6.7 | 2.0 | 7.7 | 2.8 | 14.8 | 9.4 | Increased |
| LPC (20:4) | 11.4 | 6.1 | 9.9 | 5.2 | 14.8 | 7.5 | Increased |
| LPC (22:6) | 6.3 | 2.3 | 5.2 | 1.4 | 9.6 | 8.2 | Increased |
| MG (18:1/0:0/0:0) | 6.6 | 5.3 | 13.3 | 27.1 | 85.2 | 74.6 | Increased |
| SM (d18:2/16:0) | 19.2 | 5.6 | 19.9 | 7.2 | 21.1 | 6.6 | Increased |

TABLE 5

| | | Student's t-test | | |
|---|---|---|---|---|
| Material name | Kruskal-Wallis test | Normal control group vs. acute myocardial infarction group | Normal control group vs. unstable angina group | Acute myocardial infarction group vs. unstable angina group |
| L-Tryptophan | <0.001 | 0.014 | 0.025 | 0.195 |
| L-Homoserine | 0.043 | 0.036 | 0.070 | 0.192 |
| FA (18:0) (stearic acid) | <0.001 | <0.001 | <0.001 | 0.050 |
| FA (18:1) (oleic acid) | 0.001 | 0.002 | 0.058 | 0.018 |
| FA (18:2) (linoleic acid) | 0.007 | <0.001 | 0.230 | 0.010 |
| FA (22:6) (docosahexaenoic acid) | 0.014 | 0.002 | 0.608 | 0.002 |
| PC (34:3) | 0.021 | 0.332 | 0.396 | 0.639 |
| LPC (16:0) | <0.001 | <0.001 | 0.011 | 0.003 |
| LPC (18:0) | <0.001 | <0.001 | 0.032 | 0.014 |
| LPC (20:3) | 0.010 | 0.005 | 0.134 | 0.012 |
| LPC (20:4) | 0.019 | 0.075 | 0.292 | 0.024 |
| MG (18:1/0:0/0:0) | <0.001 | 0.001 | 0.256 | 0.002 |

As seen from Table 4 and Table 5, the difference in the markers between the patient groups was identical or similar to that of Example 1 and the markers that exhibited statistical significance were identical. This means that the analysis result of Example 1 was reconfirmed in Example 2 conducted for different test participants.

Figure 9:
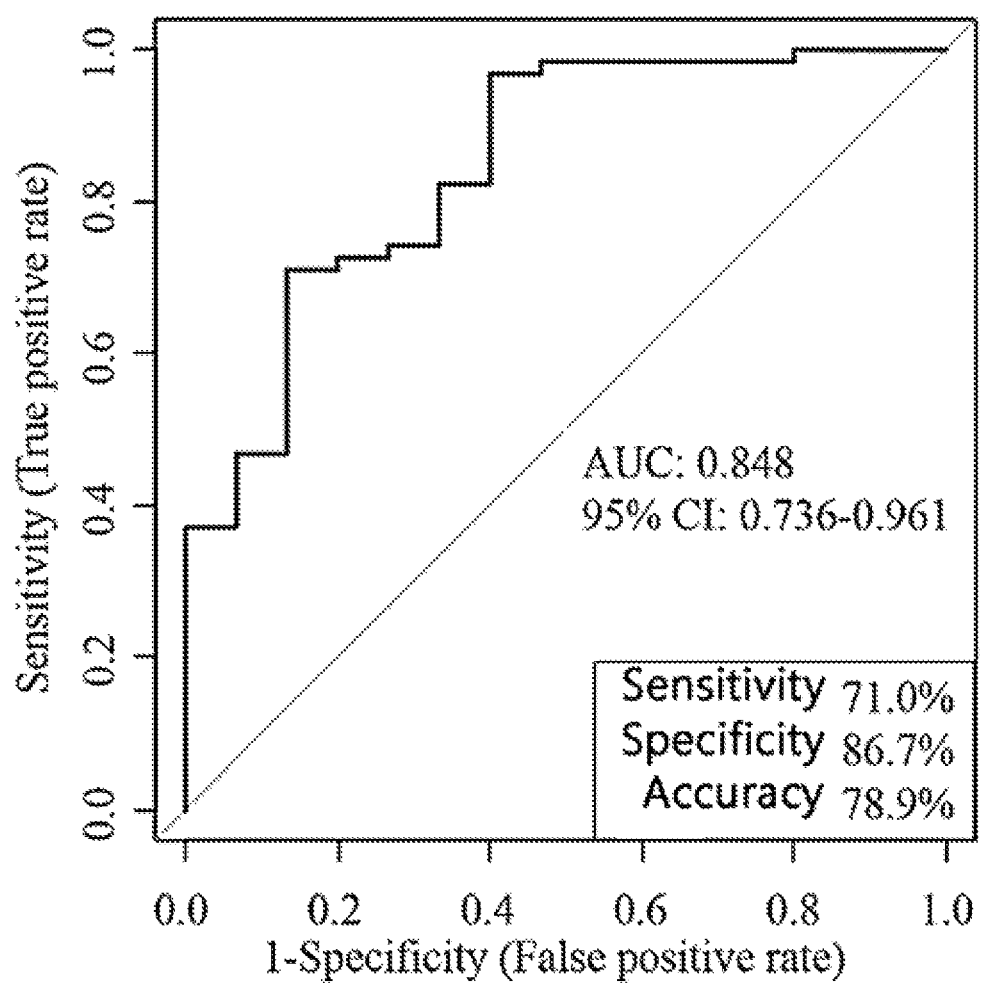
FIGS. 9-11 show results of reconfirming the results of FIGS. 2-4 in different test groups in Example 2.
Figure 10:
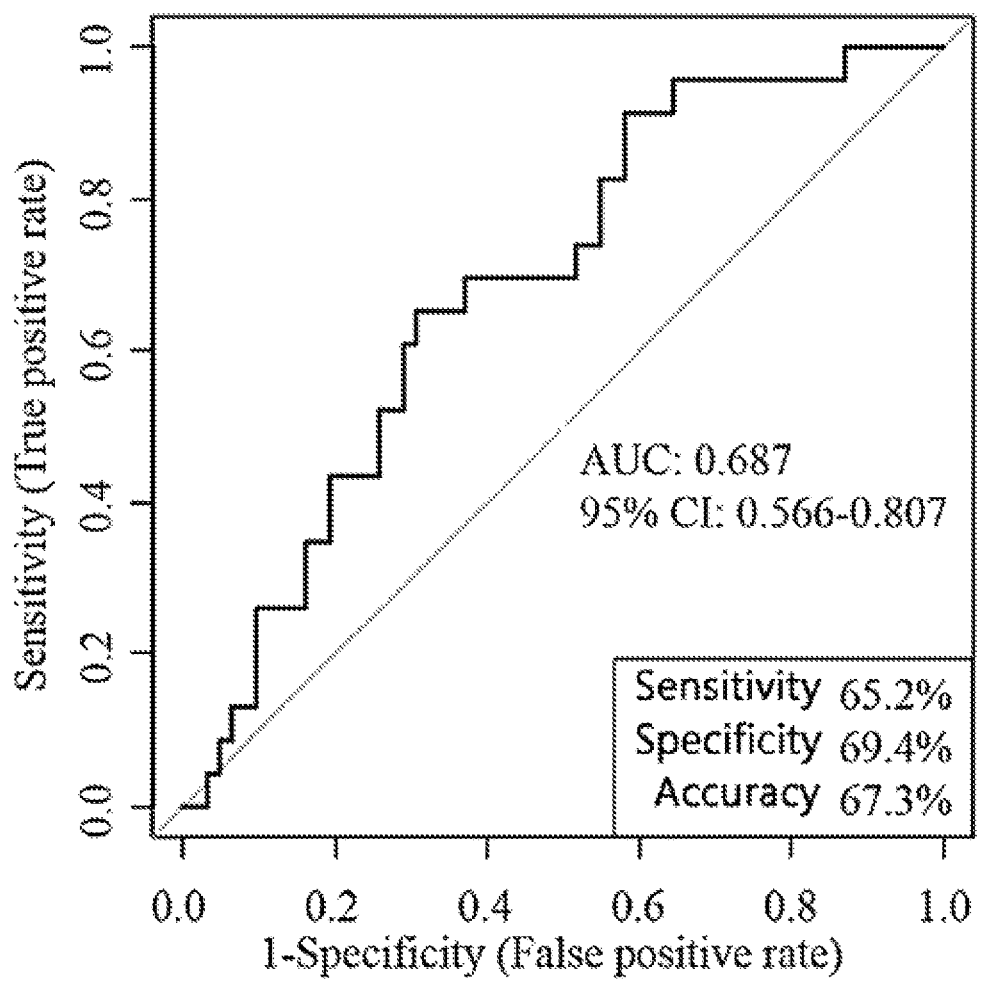
Figure 11:
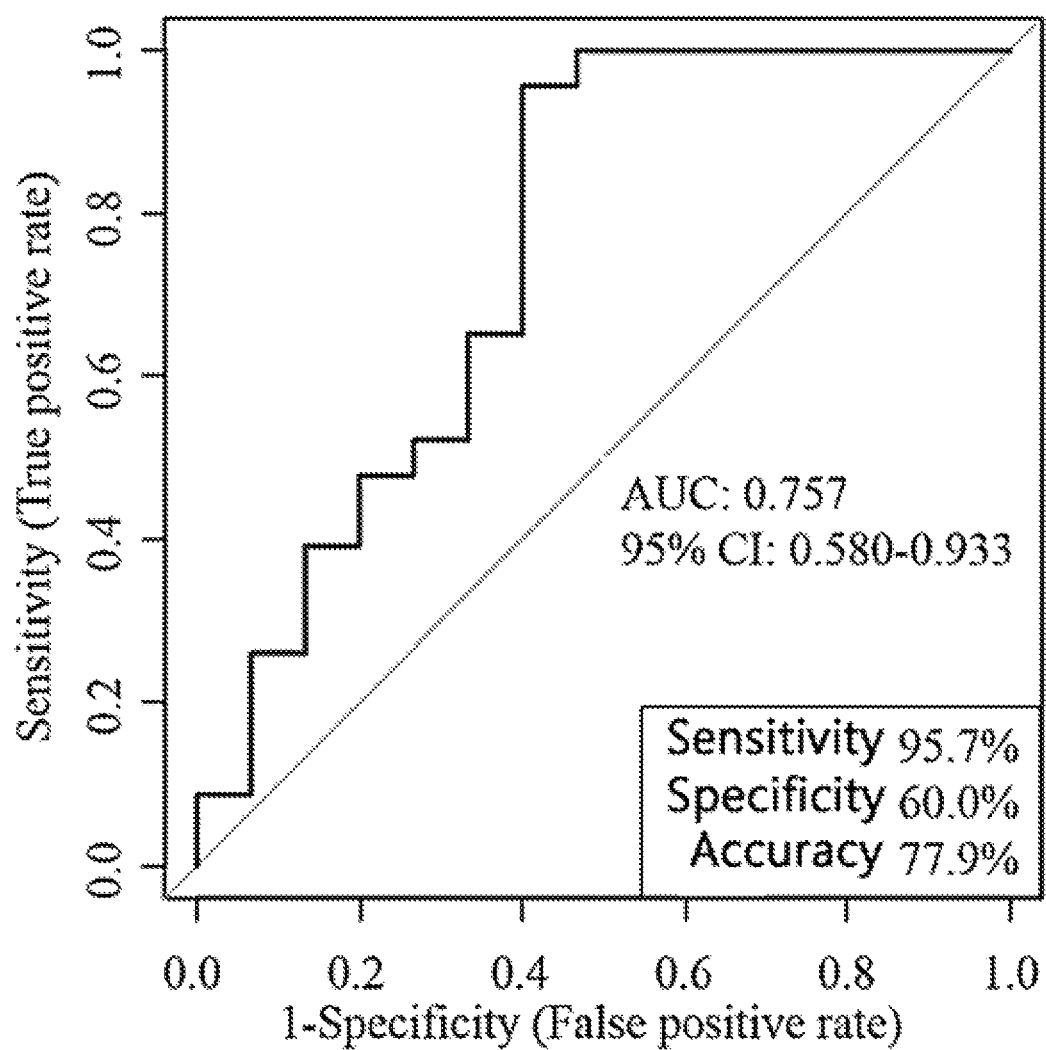
Figure 12:
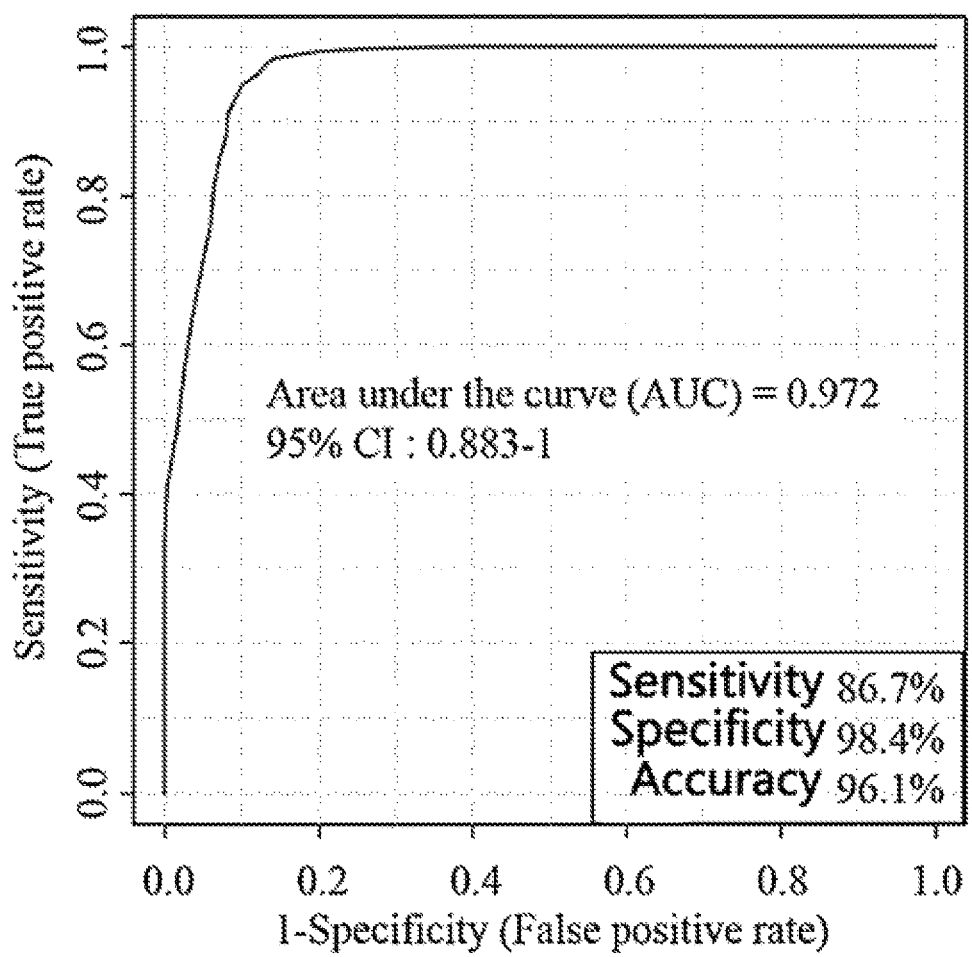
FIGS. 12-14 show results of reconfirming the results of FIGS. 5-7 in different test groups in Example 2.
Figure 13:
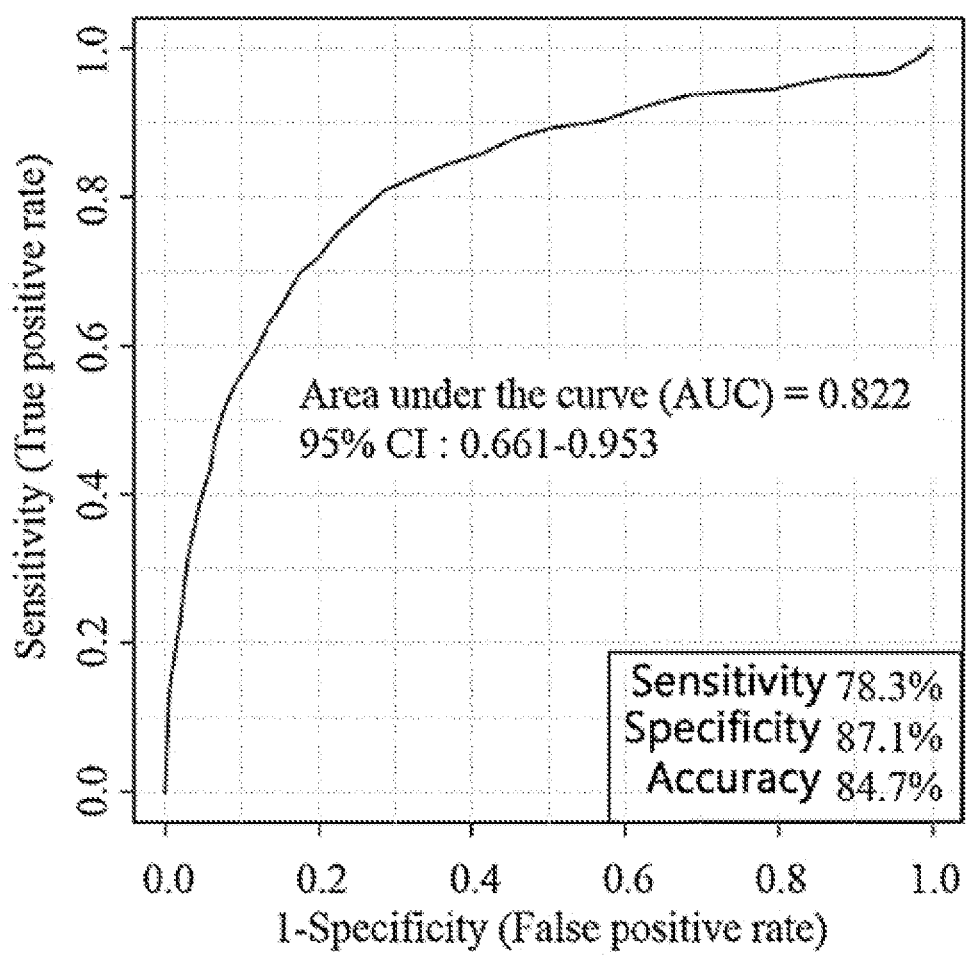
Figure 14:
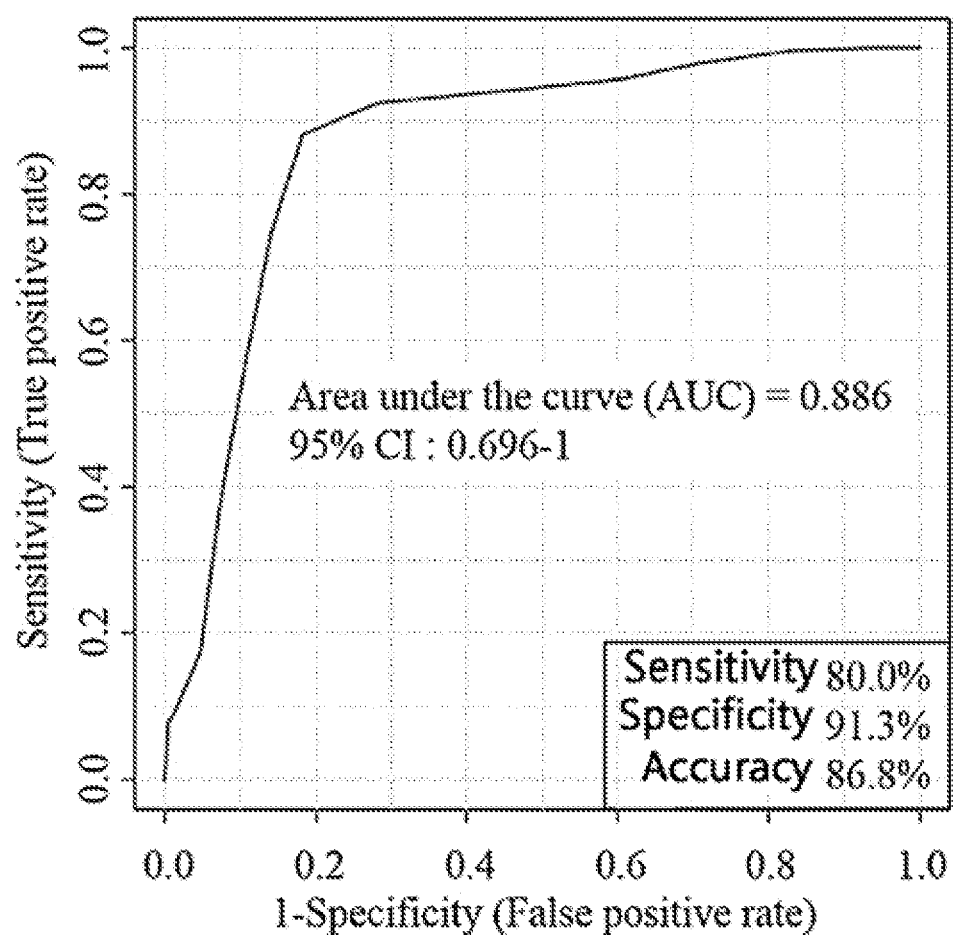

In addition, from FIGS. 9-14, it can be seen that the accuracy of multivariate analysis result using multiple metabolites (FIGS. 12-14) is about 8.9-17.4% higher as compared to that of univariate analysis result using a single metabolite (FIGS. 9-11). This reconfirms the result of Example 1 that a multivariate analysis system using multiple metabolites provides better accuracy and suggests that the multi-biomarker diagnostic platform of present disclosure is successfully validated.

What is claimed is:

1. A kit for diagnosis of acute coronary syndrome, comprising:
  a detector configured to detect in-vivo level of one or more metabolite selected from a group consisting of tryptophan, homoserine, phosphatidylcholine (PC) (34:2), PC (34:3), lysophosphatidylcholine (lysoPC) (16:

0), lysoPC (20:4), lysoPC (22:6), monoglyceride (18:1/0:0/0:0) and sphingomyelin (d18:2/16:0) from a sample, a composition comprising tryptophan, homoserine, phosphatidylcholine (PC) (34:2), PC (34:3), lysophosphatidylcholine (lysoPC) (16:0), lysoPC (20:4), lysoPC (22:6), monoglyceride (18:1/0:0/0:0) and sphingomyelin (d18:2/16:0) in a control level corresponding to normal control group of healthy people without the acute coronary syndrome;

a multivariate analysis system configured to analyze a difference in the in-vivo level of the one or more metabolite and the control level, and an instruction for an acute coronary syndrome diagnosis method, wherein the method comprises:

measuring, using the in-vivo level detector, the level of the one or more metabolite from a sample, wherein the sample comprises a biological fluid taken from a patient, to obtain a patient metabolite level; and comparing the patient metabolite level to a normal control group level of the one or more metabolite.

2. The kit for diagnosis of acute coronary syndrome according to claim 1, wherein the detector further detects in-vivo level of one or more metabolite selected from a group consisting of fatty acid (16:1), fatty acid (18:0), fatty acid (18:1), fatty acid (18:2), fatty acid (22:6), lysoPC (18:0) and lysoPC (20:3), and wherein the composition further comprises fatty acid (16:1), fatty acid (18:0), fatty acid (18:1), fatty acid (18:2), fatty acid (22:6), lysoPC (18:0) and lysoPC (20:3) in a control level corresponding to normal control group of healthy people without the acute coronary syndrome.

3. The kit for diagnosis of acute coronary syndrome according to claim 1, wherein the acute coronary syndrome comprises one or more of acute myocardial infarction and unstable angina occurring prior to the onset of acute myocardial infarction.

4. The kit for diagnosis of acute coronary syndrome according to claim 2, wherein the acute coronary syndrome comprises one or more of acute myocardial infarction and unstable angina occurring prior to the onset of acute myocardial infarction.

5. The kit for diagnosis of acute coronary syndrome according to claim 1, wherein the detector comprises a multi-metabolite detector configured to measure the in-vivo level of metabolites comprising tryptophan, homoserine, fatty acid (16:1), fatty acid (18:0), fatty acid (18:1), fatty acid (18:2), fatty acid (22:6), phosphatidylcholine (PC) (34:2), PC (34:3), lysoPC (16:0), lysoPC (18:0), lysoPC (20:3), lysoPC (20:4), lysoPC (22:6), monoglyceride (18:1/0:0/0:0) and sphingomyelin (d18:2/16:0).

6. The kit for diagnosis of acute coronary syndrome according to claim 5, wherein the acute coronary syndrome comprises one or more of acute myocardial infarction and unstable angina occurring prior to the onset of acute myocardial infarction.

7. The kit for diagnosis of acute coronary syndrome according to claim 1, wherein the multivariate analysis system is configured to diagnose as acute coronary syndrome when the in-vivo level of one or more of tryptophan, PC (34:3), lysoPC (16:0) and lysoPC (18:0) is lower as compared to the control level or when the in-vivo level of one or more of homoserine, fatty acid (16:1), fatty acid (18:0), fatty acid (18:1), fatty acid (18:2), fatty acid (22:6), PC (34:2), lysoPC (20:3), lysoPC (20:4), lysoPC (22:6), monoglyceride (18:1/0:0/0:0) and sphingomyelin (d18:2/16:0) is higher as compared to the control level.

8. A method for diagnosis of acute coronary syndrome, the method comprising:

obtaining a plasma sample from subjects by centrifugation of venous blood sample taken from a patient subject and a normal subject and placing said plasma sample for a period of time;

deproteinizing the plasma sample by pretreating with methanol;

measuring a level of one or more metabolite from the plasma sample, wherein the sample comprises a biological fluid taken from a patient, to obtain a patient metabolite level using the kit according to claim 1, wherein the one or more metabolite is selected from a group consisting of tryptophan, homoserine, phosphatidylcholine (PC) (34:2), PC (34:3), lysophosphatidylcholine (lysoPC) (16:0), lysoPC (20:4), lysoPC (22:6), monoglyceride (18:1/0:0/0:0) and sphingomyelin (d18:2/16:0);

wherein measuring the level of one or more metabolite from a sample comprises detecting the metabolite using multivariate analysis system;

comparing the patient metabolite level to a control level corresponding to normal control group of healthy people without the acute coronary syndrome using the composition according to claim 1; and diagnosing the acute coronary syndrome based on the comparison.

* * * * *